United States Patent [19]

Hughes

[11] 4,066,075
[45] Jan. 3, 1978

[54] U-SHAPE INTRAVAGINAL DEVICE

[75] Inventor: Amy Gray Hughes, Cincinnati, Ohio

[73] Assignee: The Procter & Gamble Company, Cincinnati, Ohio

[21] Appl. No.: 701,056

[22] Filed: June 30, 1976

Related U.S. Application Data

[63] Continuation-in-part of Ser. No. 578,297, May 16, 1975, abandoned.

[51] Int. Cl.² ............................................. A61F 5/46
[52] U.S. Cl. .................................... 128/127; 128/260
[58] Field of Search ............................. 128/127–131, 128/260

[56] References Cited

U.S. PATENT DOCUMENTS

| Re. 28,399 | 4/1975 | Zipper | 128/127 |
| 101,317 | 3/1870 | Schmitt | 128/127 |
| 182,437 | 9/1876 | Harding | 128/127 |
| 235,959 | 12/1880 | Otto | 128/127 |

Primary Examiner—Lawrence W. Trapp
Attorney, Agent, or Firm—Thomas J. Slone; Jerry J. Yetter; Richard C. Witte

[57] ABSTRACT

A nonobstructive U-shape intravaginal device adapted to be placed in the vagina of a female mammal so that the arcuate-shape, closed-end portion of the device is disposed in the posterior fornix of the vagina, and so that the spaced arms of the device extend generally towards the introitus of the vagina and are adjacent the lateral walls of the vagina. When thus disposed, the device does not materially obstruct the portion of the vagina anterior of the cervix uteri and thus would not be a source of interference or discomfort during sexual intercourse. The device may comprise an effective charge of such beneficial materials as medicaments, contraceptives, or deodorants or the like within a sufficiently permeable structure that the charge is released over an extended period of time by the action of body fluids on the device whereby sustained beneficial effects are achieved.

8 Claims, 14 Drawing Figures

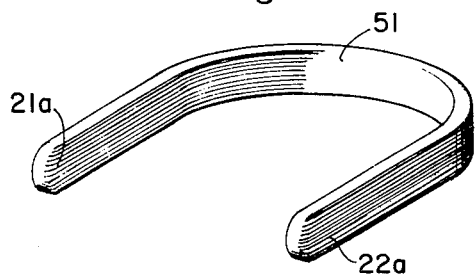
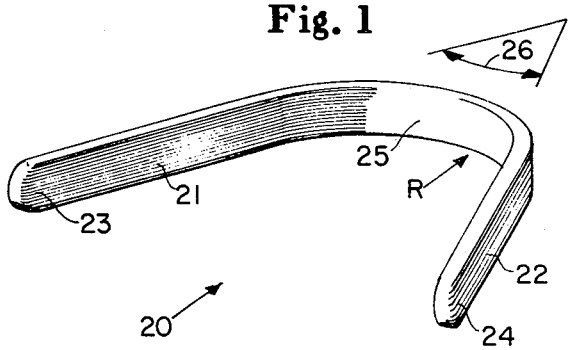
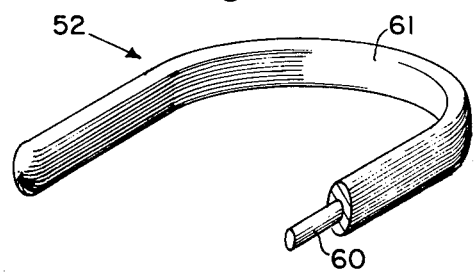
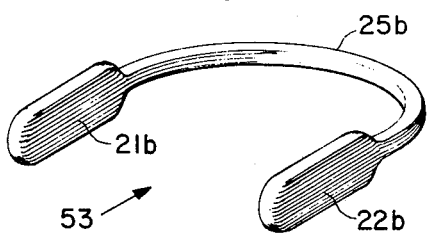
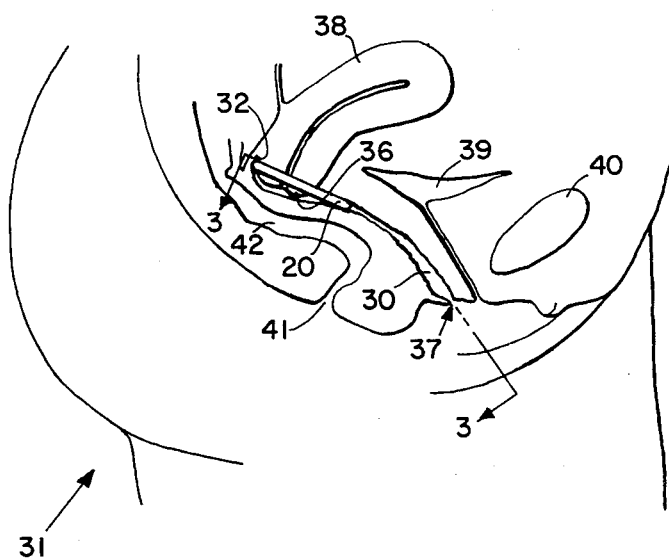
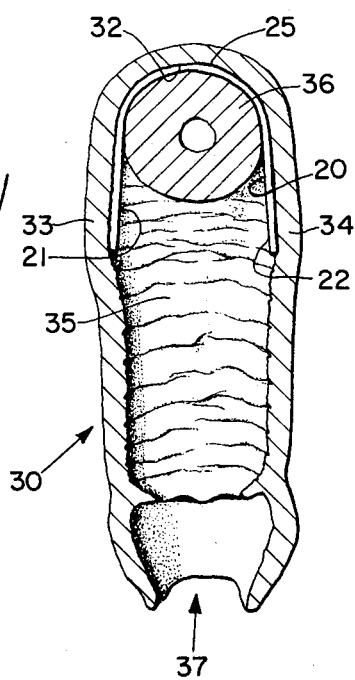

U-SHAPE INTRAVAGINAL DEVICE

CROSS-REFERENCE TO RELATED APPLICATION

This is a continuation-in-part of the abandoned co-pending application of A. G. Hughes, Ser. No. 578,297, filed May 16, 1975, entitled U-SHAPE INTRAVAGINAL DEVICE.

FIELD OF THE INVENTION

This invention relates generally to providing intravaginal devices (hereinafter IVD's) for such purposes as supporting the uterus, and/or for releasing such beneficial materials as medicaments, spermicidal and other contraceptive agents, or deodorants in the vaginas of female mammals. More specifically this invention provides IVD's having U-shape geometries which, when properly oriented, will not materially obstruct the portion of a vagina anterior of the cervix uteri so that the device does not precipitate interference or discomfort during sexual intercourse. Thus, for example, devices embodying the present invention are useful for such purposes as period-to-period contraceptives which are described more fully hereinafter.

BACKGROUND OF THE INVENTION

Pessaries and other intravaginal devices of various geometries other than the U-shape device of the present invention are known. For instance, a somewhat dome-shape vaginal diaphragm, a hemispherical-shape cervix cap, and a mushroom-shape cervix button are disclosed in FIG. 160 of the book Human Sex Anatomy by Robert Latou Dickinson, Second Edition, Copyright 1949, published by The Williams and Wilkins Company.

Vaginal diaphrams commonly comprise a toroidal ring of resilient material which ring is closed by a dome shape flexible diaphragm member. Desirably, a vaginal diaphragm is sized and applied so that it is lodged between the posterior fornix of the vagina and the pubic arch. The diaphragm is designed to physically isolate the cervix uteri from sperm by virtue of the diaphragm being above a male partner's penis during sexual intercourse. However, because of such factors as poorly defined pubic arches, poorly fitted vaginal diaphragms, and the effects of body movements and contortions, the front portion of the diaphragm may move downwardly from behind the pubic arch towards the bottom wall of the vagina whereupon the device partially obstructs the vagina. When such partial obstruction occurs, the diaphragm becomes a source of irritation or discomfort during intercourse, and the potential contraceptive efficacy of the device is compromised or vitiated.

The prior art also discloses, in U.S. Pat. No. 3,545,439 which issued Dec. 8, 1970 to Gordon W. Duncan, a toroidal-shape IVD not closed by a diaphram member. As disclosed, this device is sized and fitted similarly to vaginal diaphragms and is subject to partially obstructing the vagina as described above.

Some cervix caps are constructed similarly to vaginal diaphragms but are sized to cap the bottle-neck-shape cervix uteri which, in many human females extends downwardly into the vagina near its posterior end. When applied, an arcuate portion of the cervix cap extends around the anterior portion of the cervix uteri and is thus disposed to be contacted by a male partner during intercourse. Such contact results in some degree of unnatural sensation or discomfort to the male partner and/or the female.

Cervix buttons commonly have shafts which extend upwardly into the cervical canal for orienting and retaining the devices in the proper position. These shafts are, therefore, sources of irritation and may precipitate erosion of the inwardly facing surfaces of the cervical canal. Furthermore, because of the danger of precipitating a puncture-type wound, such cervix buttons are normally required to be inserted by physicians.

The prior art further includes pessaries of other shapes which are intentionally disposed and configured to be contacted by a male partner during sexual intercourse. Necessarily, such pessaries precipitate unnatural sensations and/or a degree of discomfort to one or both partners. Such pessaries are shown for example in U.S. Pat. No. 3,683,904 which was issued Aug. 15, 1972 to Howard B. Forster.

However, none of the discovered prior art discloses an intravaginal device which solves the problems of intravaginal devices described above in the manner of or to the degree of the present invention.

OBJECTS OF THE INVENTION

The nature and substance of the invention will be more readily appreciated after giving consideration to its major aims and purposes. The principal objects of the invention are recited in the ensuing paragraphs in order to provide a better appreciation of its important aspects prior to describing the details of a preferred embodiment in later portions of this description.

A major object of the invention is providing an intravaginal device having a geometry which enables the device to be worn in female mammals for extended periods of time without substantially obstructing the portion of the female's vagina anterior the cervix uteri, or precipitating unnatural sensations or discomfort during sexual intercourse.

Another object of the invention is providing an intravaginal device as described in the preceeding paragraph which comprises a predetermined charge of a beneficial material, and means for releasing the charge over an extended period of time to achieve sustained beneficial results.

Still another object of the present invention is providing an intravaginal device as described in the two preceeding paragraphs which device is particularly well suited for use in female mammals, especially human females, wherein the axis of the uterus intersects the axis of the vagina at a sufficiently large angle, and wherein the cervix uteri extends into the vagina sufficiently close to the posterior wall of the vagina to define an arcuate-shape vault or posterior fornix intermediate the posterior wall of the vagina and the adjacent portion of the cervix uteri.

Yet still another object of the present invention is providing a U-shape intravaginal device having a heel portion adapted to provide mechanical support to at least a posterior portion of the cervix uteri when the closed portion of the U-shape device is disposed adjacent the posterior wall of the vagina of a female mammal such as a human female.

SUMMARY OF THE INVENTION

The above and other objects are achieved by providing a U-shape intravaginal device comprising two arms and an arcuate portion which are secured together in end-to-end relation. The device is sized and configured so that the arcuate-shape portion of the device can be accomodated in the arcuate-shape vault intermediate the posterior wall of the vagina and the adjacent portion of the cervix uteri of female mammals having such vaults, and so that the arms of the device extend generally towards the introitus of the vagina and are disposed adjacent the lateral walls of the vagina. The device may comprise resilient material so that the arms are biased outwardly against the lateral walls of the vagina. The device may further comprise a predetermined charge of a beneficial material, and means for releasing the charge over an extended period of time after the device has been inserted into the vagina of a female mammal to achieve sustained beneficial results.

BRIEF DESCRIPTION OF THE DRAWINGS

While the specification concludes with claims particularly pointing out and distinctly claiming the subject matter regarded as forming the present invention, it is believed the invention will be better understood from the following description taken in conjunction with the accompanying drawings in which:

FIG. 1 is a perspective view of a preferred embodiment U-shape intravaginal device having divergent arms.

FIG. 2 is a fragmentary median sectional view of a human female's pelvis and some contents thereof with a U-shape intravaginal device of the configuration shown in FIG. 1 disposed in the vagina.

FIG. 3 is an enlarged scale, fragmentary sectional view taken along line 3—3 of FIG. 2.

FIGS. 4 through 9 and 11 are perspective views of alternate embodiment U-shape intravaginal devices.

DESCRIPTION OF THE PREFERRED EMBODIMENT

Figure 7:
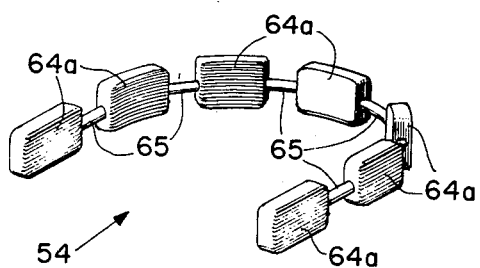

Referring now to the figures, FIG. 1 is a perspective view of an IVD 20 which is a preferred embodiment of the present invention which comprises two arms 21, 22 having distal ends 23, 24 respectively, and an arcuate-shape portion or heel 25.

Briefly, the preferred embodiment IVD 20, FIG. 1, comprises a resilient, unitary structure of silicone rubber wherein the arms 21, 22 are disposed in divergent relation with an included angle 26 therebetween. The IVD 20 is sized and configured to be placed in the vagina 30 of a female mammal such as the human female 31 shown in FIG. 2 so that heel 25 is disposed in the posterior fornix 32 of the vagina 30, and so that the arms 21, 22 are lightly biased against the lateral walls 33, 34 of the vagina 30, FIG. 3. When thus disposed in a vagina 30, the IVD 20 leaves the anterior portion 35 of the vagina intermediate the cervix uteri 36 and the introitus 37 substantially unobstructued so that the IVD does not precipitate any substantial discomfort or unnatural sensations during sexual intercourse. By virtue of its relatively non-obstructing geometry, IVD 20 can be worn for extended periods of time such as from the termination of one menstrual discharge to the beginning of the next successive discharge. This extended period of time is hereinafter referred to as period-to-period.

Referring again to FIG. 1, IVD 20 further comprises a predetermined charge (not shown) of a beneficial material impregnated in the structure, and means (not shown) for releasing the charge over an extended period of time by the action of body fluids while disposed in a vagina.

Beneficial materials, as the term is used herein, include but are not limited to medicaments, spermicidal and other contraceptive agents, fertility enhancing agents, deodorants, and other agents which are soluble in body fluids.

The means of IVD 20, FIG. 1, for releasing the charge of the beneficial material may be, for example, simply an open pored structure having the beneficial material disposed in its pores so that body fluids dissolve and leach or flush the beneficial material from the pores of the IVD into the vaginal cavity. Another means for releasing a charge of beneficial material is described more fully hereinafter in conjunction with describing the alternate embodiment IVD shown in FIGS. 9 and 10.

Still referring to FIG. 1, IVD 20 has a substantially rectangular cross-sectional shape and the distal ends 23, 24 are somewhat rounded. It is intended, however, that the device have sufficiently rounded edges to obviate punctures, cuts, and erosion within the vaginal cavity.

The angle 26, FIG. 1, between arms 21, 22 is, to some extent, a function of the structural resilience of IVD 20, and the shape differences among vaginas of female mammals. It is necessary, however, that the structural resilience and angle 26 of IVD 20 be sufficiently great, that the span intermediate distal ends 23, 24 be at least as great as the adjacent portion of the vagina so that the device will not rotate about the axis of the cervix uteri to partially obstruct the vagina. Moreover, radius R of heel 25, FIG. 1, is preferably about the radius of the posterior portion of the cervix uteri 36, FIG. 3, so that the posterior fornix 32 is not unduly distorted by the presence of an IVD in the orientation shown in FIGS. 2 and 3.

FIG. 2 is a fragmentary median sectional view of a human female's pelvis in the standing position with an IVD 20 disposed in the vaginal cavity. The female's vagina 30, introitus 37, posterior fornix 32, uterus 38, cervix uteri 36, bladder 39, symphysis 40, anus 41, and rectum 42 are identified in FIG. 2 to enable understanding the preferred orientation of an IVD 20 in the vagina 30.

As shown in FIG. 2, the portion of the uterus 38, adjacent the closed end of the vagina 30, intersects the posterior portion of vagina 30, at about a right angle, more-or-less, and the bottle-neck-shape cervix uteri 36 extends somewhat downwardly into vagina 30. This relationship which is representative of normal human females defines an arcuate-shape vault intermediate the posterior wall of the vagina 30, and the adjacent portion of the cervix uteri 36, which vault is named the posterior fornix 32.

Still referring to FIG. 2, the relaxed vagina 30, has a somewhat elongate S-shape profile intermediate the posterior fornix 32 and the introitus 37. The significance of this S-shape profile will be described hereinafter in conjunction with describing the articulated alternate embodiment, U-shape IVD's shown in FIGS. 7 and 8.

FIG. 3 is an enlarged scale, sectional view of the vagina 30 and the cervix uteri 36 of a human female 31 which view was taken along line 3—3 of FIG. 2. An IVD 20 is shown in FIG. 3 with the heel 25 of the IVD disposed in the posterior fornix 32 of vagina 30 and with the arms 21, 22 of the IVD lightly biased oppositely against the lateral walls 33, 34 of vagina 30. This is the preferred orientation of IVD 20 and assures that the anterior portion 35 of the vagina is virtually unobstructed by the IVD and thus would not precipitate discomfort or unnatural sensations during sexual intercourse.

ALTERNATE EMBODIMENTS

Alternate embodiment U-shape intravaginal devices (IVD's) 51 through 58 are shown in FIGS. 4 through 14. All of the alternate embodiment IVD's 51-58 comprise, in a broad sense, two arms, and an arcuate-shape heel similarly disposed and related to each other as the arms 21, 22 and the heel 25 of the preferred embodiment IVD 20, FIG. 1. Therefore, to simplify the descriptions of the alternate embodiment IVD's, only their significant differences will be described.

FIG. 4 shows an alternate embodiment IVD 51 having substantially parallel arms 21a and 22a. For any given material of construction, for instance silicone rubber, this geometry would probably require more careful fitting to individual users to obviate its being closed by tensioning of the vaginal walls.

FIG. 5 shows alternate IVD 52 having a stiffener member 60 molded into a unitary U-shape structure 61 having an oval cross-sectional shape. The stiffener 60 is a means for increasing the resistance of the IVD to being closed. That is, the stiffener increases the spring constant of the structure with respect to forces which would tend to move the free ends of the arms together.

FIG. 6 shows alternate IVD 53 comprising two paddle-shape arms 21b, 22b, joined together by an arcuate-shape, tether-like heel 25b to form the U-shape IVD 53. The small cross section of the tether-like heel 25b enables this device to easily conform to a range of vaginal and posterior fornix geometries of a population of users.

Figure 8:
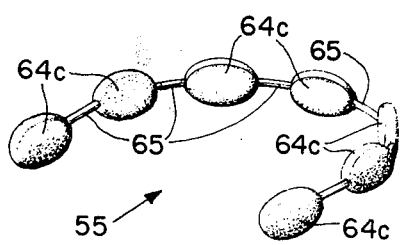

FIGS. 7 and 8 show alternate embodiment IVD's 54 and 55 respectively which are articulated assemblies of button-like members 64a, 64c, and coupling members 65. The button-like members 64a of IVD 54 are generally parallelopipedal shapes and members 64c of IVD 55 are oval shape.

Articulated IVD's such as IVD's 54 and 55, FIGS. 7 and 8, are particularly useful in human females wherein the S-shape profile of the vagina, FIG. 2, is very pronounced. An articulated IVD will conform to the curvature of such vaginal cavities rather than exert discomforting or deleterious forces on the vaginal walls which would tend to straighten out the S-shape curvature.

Figure 9:
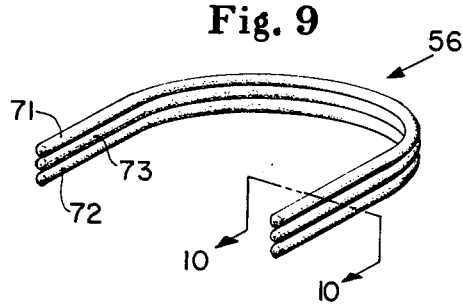
Figure 10:
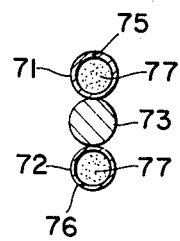
FIG. 10 is a sectional view taken along line 10—10 of FIG. 9.

IVD 56, FIGS. 9 and 10, is a U-shape assembly comprising a plurality of tubular shape members which plurality as shown is three in number and the members are designated 71, 72 and 73. At least one of these members comprises the alternate means for releasing a charge of beneficial material which was referred to hereinbefore.

Briefly, the alternate release means comprises a container having a permeable wall portion, and a predetermined quantity or charge of a body-fluid-soluble beneficial material disposed in the container. For instance, the permeable wall portion can be regenerated cellulose which is permeable by human body fluids, and the beneficial material can be a micelleforming surfactant compound which is soluble in human body fluids. When acted on by human body fluids, such a container becomes pressurized through osmosis, and dispenses the surfactant at a controlled rate so that beneficial results are achieved over a prolonged period of time.

Referring back to FIG. 10, IVD 56 comprises two tubular members or containers 71, 72 having permeable walls 75, 76 respectively, and each contains a charge of beneficial materials 77 as described above. IVD 56 further comprises a form-sustaining, U-shape tubular member 73 which is secured (by means not shown) to the tubular containers 71, 72 to assure the desired U-shape geometry of the IVD. Of course, in the event that the tubular containers 71, 72 have sufficient structural integrity, the need for the form-sustaining member 73 would be obviated.

Figure 11:
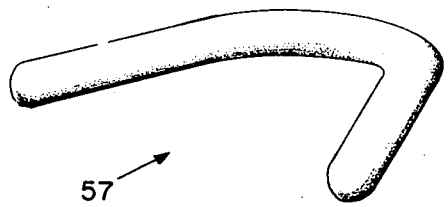

IVD 57, FIG. 11, is substantially like IVD 20, FIG. 1, but for comprising a U-shape tubular body having a circular cross-section as opposed to a rectangular cross-section.

Figure 12:
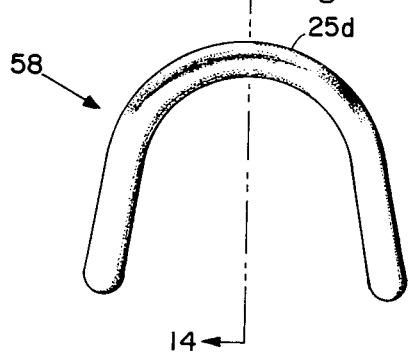
FIG. 12 is a plan view of yet another alternate embodiment U-shape intravaginal device.
Figure 13:
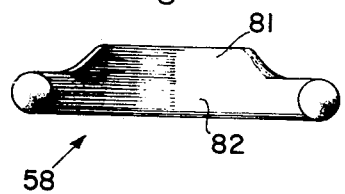
FIG. 13 is a frontal view of the alternate embodiment U-shape intravaginal device shown in FIG. 12.
Figure 14:
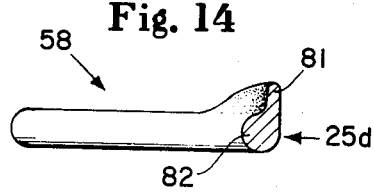
FIG. 14 is a sectional view taken along line 14—14 of FIG. 12.

FIGS. 12-14 inclusive show an alternate embodiment U-shape IVD 58 having a heel 25d which comprises an upwardly extending arcuate shape rim 81 and a radially inwardly extending arcuate-shape support portion 82. The rim 81 is configured to fit the user's posterior fornix and the support portion 82 is adapted to provide mechanical support for the posterior portion of the user's cervix uteri. Thus, this configuration IVD is useful as a support pessary as well as, if provided with a charge of beneficial material, for applying the beneficial material to a vaginal cavity as described hereinbefore.

As noted hereinabove, preferred devices having the novel conformations disclosed herein comprise an effective charge of beneficial materials such as medicaments, contraceptives, deodorants, and the like, most preferably within a sufficiently permeable structure that the charge is released over an extended period of time by the action of body fluids on the device, whereby sustained beneficial effects are achieved. Similarly, various beneficial agents can be releasably affixed to the outer surfaces of the articles herein to provide various desirable biological responses.

Typical examples of biologically active agents which can be used in and/or on articles having the conformation described herein and especially adapted for use in the vagina include:

1. Bacteria-controlling agents such as the antibiotics, e.g., the penicillins, the cephalosporins, the tetracyclines, the aureomycins, the streptomycins and the pharmaceutically-acceptable salts thereof, as well as the polymyxins, the chloramphenicols, and the sulfonamides.

2. Fungi-controlling agents such as the griseofulvins, the odd-chain fatty acids, or the pharmaceutically-acceptable salts thereof, e.g., zinc undecylenate.

3. Anti-inflammatories such as hydrocortisone, cortisone, fluocinolone, triamcinolone, prednisolone, and the salts thereof.

4. Estrogens such as diethyl stilbestrol and the prostaglandins such as $PGE_1$, $PGE_2$ and $PGF_2\alpha$.

5. Pharmacologically-safe acids which temporarily lower the pH of vaginal fluids and/or cervical mucus, such as tartaric acid, citric acid, boric acid, and the like.

6. Various microbiocides such as phenylmercuric chloride, benzethonium chloride, methyl benzethonium chloride, oxyquinoline sulfate, sodium N,N-dichlorosulfonamidobenzoate, and the like.

7. Lubricants such as cocoa butter, petrolatum, and the like.

8. Spermicidal surfactants, especially the alkylene oxide nonionic surfactants. Such materials include the well-known condensation products of polyethylene oxide with an alcohol or alkyl phenol. Specific examples of such spermicides include nonylphenol pentaethoxylate, nonylphenol octaethoxylate, nonylphenol nonaethoxylate, n-dodecanol octaethoxylate, and the like. Such materials can be releasably absorbed into articles of the present type, especially those articles prepared from medical grade silicone and latex rubber.

9. Nonionic alkylene oxide spermicidal surfactants in aqueous solution and releasably held in containers with semi-permeable membrane walls. Such surfactants include, for example, aqueous solutions of $C_{10}H_{21}(OCH_2CH_2)_5OH$ and $C_{10}H_{21}(OCH_2CH_2)_6OH$ releasably contained within a thin, cellulose-walled container, all as described in the copending application of R. G. Laughlin, Ser. No. 560,020, filed Mar. 19, 1975, P&G Attorney's Docket No. 2186, the disclosures of which are incorporated herein by reference.

The cellulose membrane used in the walls should be of a thickness (wet) less than about 150 microns ($\mu$) and is most preferably about 25–50$\mu$ thick (wet). Cellulose membranes thicker than about 150$\mu$ (wet) tend to impede release of surfactant monomer, whereas thicknesses below ca. 5–10$\mu$ (wet) cause the walls of the containers to be subject to osmotic rupture even by the relatively low osmotic pressures of the concentrated surfactant solutions.

Containers comprising cellulose walls can be prepared in the manner disclosed by Laughlin, above, by casting membranes from solutions of cellulose acetate in an organic solvent, allowing the solvent to evaporate, and deacetylating with aqueous ammonia to regenerate the cellulose. The containers are then charged with an aqueous solution of nonionic surfactant, and surfactant monomers are slowly released through the cellulose walls to the vagina to provide a contraceptive effect.

The following examples illustrate preferred controlled and sustained release articles of the present type.

EXAMPLE I

A flat sheet of commercial cellulose acetate about 75$\mu$ thick and measuring about 7 in. × 10 in. is subjected to thermoforming methods known in the art to produce minute hemispherical identations in the sheet. These indentations are filled to ca. 25% of their total volume with pure $C_{10}H_{21}(OCH_2CH_2)_5OH$ surfactant. A second flat sheet of cellulose acetate film is solvent-sealed (acetone) over the original sheet covering the indentations using techniques known in the art.

The individual, filled and sealed indentations are then cut from the composite sheet to provide "bubbles" which are then immersed in a 7.4 M ammonia solution containing 10% by weight sodium chloride for 96 hours at 50° C. This ammonia treatment regenerates the cellulose by deacetylating the cellulose acetate. Water passes through the membrane under the influence of osmotic forces during the deacetylation, partially filling the sealed bubble-shaped containers.

Following the ammonia treatment, the containers are immersed in distilled water, whereupon they fill completely under the influence of osmosis, the entrapped air diffusing out leaving containers consisting of regenerated cellulose enclosing a ca. 25% solution of the $C_{10}H_{21}(OCH_2CH_2)_5H$ surfactant.

A plurality of the bubble-shaped containers prepared in the foregoing manner are permanently sealed with adhesive to the outer surfaces of any of the IVD articles herein, corresponding to FIGS. 1, 4, 5, 6, 7, 8, 9, 11 and 12, respectively.

An article of the foregoing type is placed in the vagina posterior to the introitus. The article is worn during the time between menses and safely delivers a spermicidally effective amount of the surfactant to the vaginal area.

In the article of Example I the $C_{10}H_{21}(OCH_2CH_2)_5OH$ is replaced by an equivalent amount of $C_{10}H_{21}(OCH_2CH_2)_6OH$ and equivalent results are secured.

In the article of Example I the pure pentaethoxylated surfactant is replaced by an equivalent amount of a 90:10 (wt.) mixture of the penta- and hexa-ethoxylated surfactant and good spermicidal activity over about a 21-day period is secured.

EXAMPLE II

Medical grade polydimethylsilicone rubber is submerged in liquid n-$C_{10}H_{21}(OCH_2CH_2)_5OH$ surfactant overnight. The silicone rubber absorbs ca. 10% of its weight of the nonionic surfactant.

Silicone rubber charged with the n-$C_{10}H_{21}(OCH_2CH_2)_5OH$ surfactant in the foregoing manner is fashioned into the configuration of any one of the articles corresponding to FIGS. 1, 4, 5, 6, 7, 8, 9, 11 and 12 herein, respectively.

An article of the foregoing type is placed in the vagina posterior to the introitus. The article is worn during the time between menses and delivers a spermicidally effective amount of the surfactant to the vaginal area.

What is claimed is:

1. A U-shape intravaginal device for use in female mammals in which an arcuate-shape vault is defined intermediate the posterior wall of the vagina and the adjacent portion of the cervix uteri of the female, said device comprising two arms and an arcuate-shape heel, said arms and said heel being secured together in end-to-end relation with said heel portion disposed intermediate said arms, said heel of said device being configured to be accommodated in said arcuate-shape vault so that said arms of said device extend generally towards the introitus of said vagina and are disposed adjacent the lateral walls of said vagina, said heel further comprising an upwardly extending arcuate-shape rim, and a radially inwardly extending arcuate-shape support portion, said rim being sized and configured to fit a user's posterior formix, and said support portion being configured and adapted to mechanically support a posterior portion of the user's cervix uteri.

2. The U-shape intravaginal device of claim 1 further comprising a predetermined charge of a beneficial material and means for releasing said charge over an extended period of time after said device has been inserted into the vagina of a female mammal.

3. The article of claim 2 wherein the beneficial material is a spermicidal surfactant.

4. The article according to claim 3 wherein the spermicidal surfactant is a nonionic alkylene oxide surfactant.

5. The article according to claim 4 wherein the alkylene oxide surfactant is selected from $C_{10}H_{21}(OCH_2CH_2)_5OH$ and $C_{10}H_{21}(OCH_2CH_2)_6OH$.

6. The article according to claim 5 wherein the surfactant is releasably contained in cellulose-walled containers affixed to said article.

7. The U-shape intravaginal device of claim 1 wherein said arms comprise sufficiently resilient material and are disposed in sufficiently divergent relation when unstressed so that when said device is disposed in a human female's vagina with said heel portion positioned intermediate the posterior wall of the vagina and the adjacent portion of said female's cervix uteri, said arms extend along and are lightly biased outwardly by their resilience against the lateral walls of the vagina whereby the portion of the vagina anterior of the cervix uteri is substantially unobstructed by said device.

8. The U-shape intravaginal device of claim 7 wherein said heel also comprises resilient material and the free-body radius of said heel is about equal to the radius of said arcuate-shape vault.

* * * * *